United States Patent
Oerter

(10) Patent No.: US 10,918,850 B2
(45) Date of Patent: Feb. 16, 2021

(54) BLOCKING AND/OR RESTRICTING VALVE AND BLOOD TREATMENT DEVICE COMPRISING SUCH A VALVE

(71) Applicant: FRESENIUS MEDICAL CARE DEUTSCHLAND GMBH, Bad Homburg (DE)

(72) Inventor: Goekhan Oerter, Weilmuenster (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/061,069

(22) PCT Filed: Dec. 8, 2016

(86) PCT No.: PCT/EP2016/002067
§ 371 (c)(1),
(2) Date: Jun. 11, 2018

(87) PCT Pub. No.: WO2017/097419
PCT Pub. Date: Jun. 15, 2017

(65) Prior Publication Data
US 2018/0353745 A1    Dec. 13, 2018

(30) Foreign Application Priority Data
Dec. 11, 2015   (DE) .................. 10 2015 016 023

(51) Int. Cl.
A61M 39/24     (2006.01)
A61M 39/22     (2006.01)

(52) U.S. Cl.
CPC .......... *A61M 39/24* (2013.01); *A61M 39/227* (2013.01); *A61M 2039/242* (2013.01);
(Continued)

(58) Field of Classification Search
CPC ............ A61M 39/24; A61M 2039/242; A61M 2039/2486; A61M 1/3672; A61M 39/227; A61M 2039/246; A61M 2039/2433
(Continued)

(56) References Cited

U.S. PATENT DOCUMENTS 2,675,758 A * 4/1954 Hughes ................... F04B 9/127
                                                      417/395
3,175,473 A * 3/1965 Boteler ................... F15B 15/10
                                                       92/128

(Continued)

FOREIGN PATENT DOCUMENTS

DE        10053441      5/2002
DE      102008061753    6/2010
(Continued)

*Primary Examiner* — Umashankar Venkatesan
(74) *Attorney, Agent, or Firm* — Jacobson Holman, PLLC

(57) ABSTRACT

The invention relates to a blocking and/or restricting valve having a valve housing which has a fluid system having a fluid inlet, a fluid outlet and a fluid chamber arranged therebetween, wherein the fluid chamber comprises a blocking geometry and is bounded by a barrier membrane with respect to the blocking geometry, wherein the barrier membrane is connected to a tappet on its side remote from the fluid chamber (8) such that it can be pressed toward the blocking geometry by a movement of the tappet and can be lifted thereby, and wherein the tappet is arranged in a freely floating manner in a hollow space of the valve housing.

9 Claims, 2 Drawing Sheets

Figure 1:
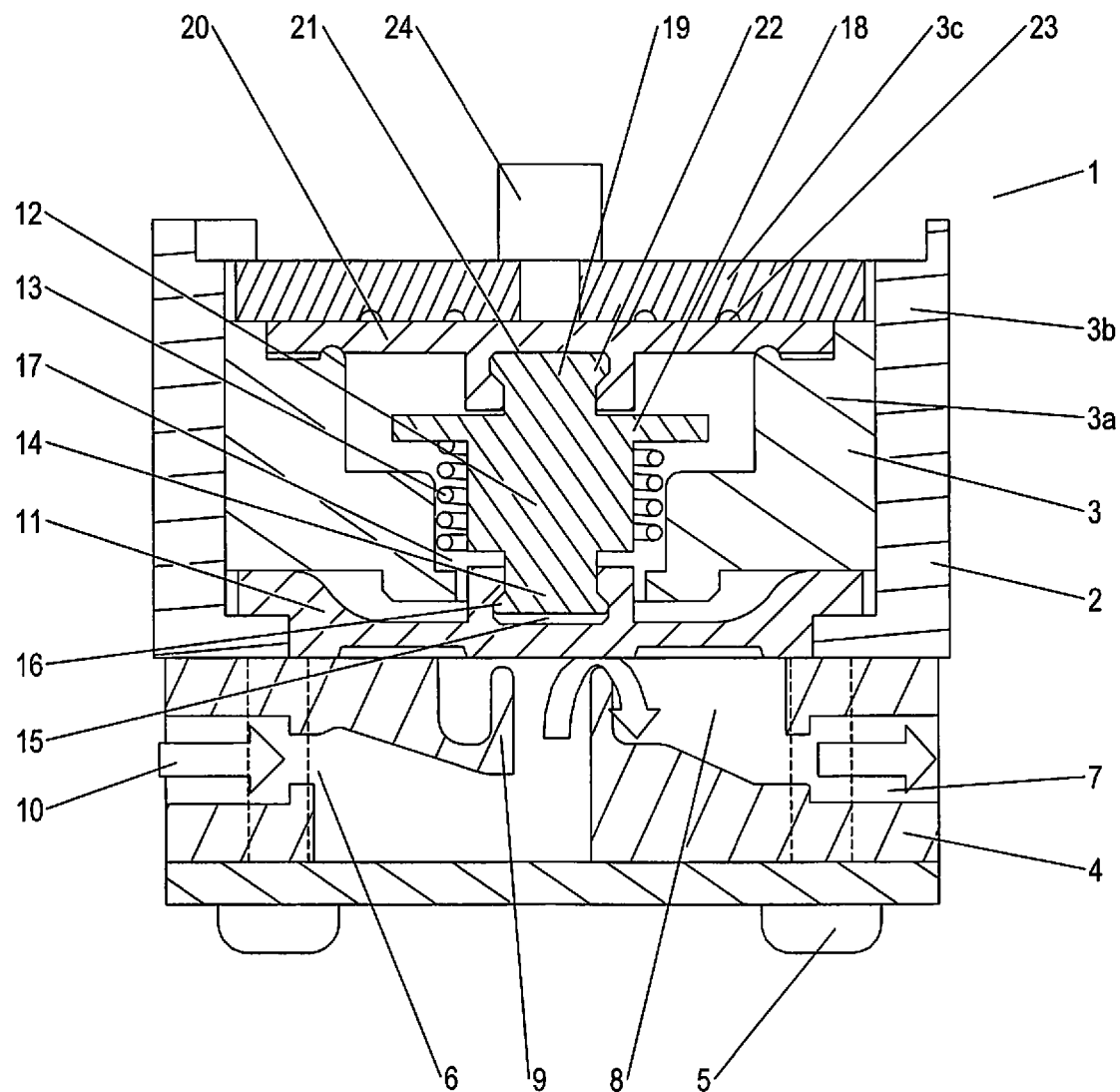

(52) U.S. Cl.
CPC ............... *A61M 2039/2433* (2013.01); *A61M 2039/2486* (2013.01)

(58) Field of Classification Search
USPC ......................................................... 251/331
See application file for complete search history.

(56) References Cited

U.S. PATENT DOCUMENTS

| | | |
|---|---|---|
| 4,630,642 A | 12/1986 | Detweiler |
| 6,308,737 B1 * | 10/2001 | Krivitski ............... A61M 1/367 137/597 |

FOREIGN PATENT DOCUMENTS

| | | |
|---|---|---|
| EP | 1897585 | 3/2008 |
| EP | 2395269 | 12/2011 |
| WO | WO 2009/029751 | 3/2009 |
| WO | WO 2015/075158 | 5/2015 |

* cited by examiner

BLOCKING AND/OR RESTRICTING VALVE AND BLOOD TREATMENT DEVICE COMPRISING SUCH A VALVE

The invention relates to a blocking and/or restricting valve and to a blood treatment device having at least one such valve.

The correct metering of fluids is of central importance in dialysis. Large fluid flows such as the flow of dialysis fluid are often conveyed via balancing systems. Medium-sized fluid flows such as the extracorporeal blood flow are often conveyed by hose roller pumps. Flow errors of up to approximately 10% are accepted in this respect.

There is, however, a higher demand on metering accuracy on the metering in of small quantities of an active agent solution, for example on the metering of an anticoagulant solution into the extracorporeal blood circuit. The flow error should in this respect be below 5% in every case. Hose roller pumps or syringe pumps are often used for this purpose in the prior art. The use of membrane pumps is, in contrast, not very prevalent in the prior art since unwanted flow pulses are generated.

The flow pulses are due to the fact that in real membrane pumps the membrane influences the pressure balance which is ideally present between the two chambers of the membrane pump due to its elasticity, due to its deformation and due to its initial tension. The relationship $P_{PNEU}=P_{HYD}=P_{MEM}$ applies to a pneumatic membrane pump in a static case. The membrane pressure $P_{MEM}$ is not constant and represents an interference factor in the regulation of the pump since the fluid pressure $P_{HYD}$ does not vary in proportion with the regulation pressure $P_{PNEU}$. The influence of this interference factor is large in a relative aspect when the fluid pressure $P_{HYD}$ and the regulation pressure $P_{PNEU}$ are low. This is the case, for example, when small flow rates are to be generated using the membrane pump.

However, a constant flow above all has to be maintained on the administration of citrate as the anticoagulant.

A blocking and/or restricting valve downstream of the pump could generally be used for smoothing the flow. Known valves of this kind are, however, only suitable for such applications with restrictions since dynamic friction effects such as a delayed response and a disproportional behavior of the valve tappet can occur in response to control ("stick-slip" phenomena).

Against this background it is the aim of the invention to provide a blocking valve in which no dynamic friction effects occur which can be regulated in a proportional manner.

Against this background, the invention relates to a blocking and/or restricting valve having a valve housing which has a fluid system with a fluid inlet, a fluid outlet and a fluid chamber arranged therebetween. The fluid chamber comprises a blocking geometry and is bounded by a barrier membrane at a side disposed opposite the blocking geometry. In accordance with the invention, the valve is characterized in that the barrier membrane is connected to a tappet at its side remote from the fluid chamber such that it can be pressed onto the blocking geometry by a movement of the tappet and can be lifted by said blocking geometry. Provision is made in this respect in accordance with the invention that the tappet is arranged floating freely in a hollow space of the valve housing.

A freely floating support of the tappet is to be understood as a frictionless support in which the surface of the tappet does not slide along a stationary element of the valve housing such as a seal and does not rub against it on a movement of the tappet.

In an embodiment, a mechanical spring is arranged between the tappet and the valve housing, the mechanical spring being able to form the bearing for the freely floating tappet and pre-loading the tappet against the valve housing such that it presses the barrier membrane toward the blocking geometry in its zero position. The valve can furthermore have an actuator which acts on the tappet and which is configured such that it can move the tappet out of the zero position against the pre-load of the mechanical spring and can thus release the barrier membrane from the blocking geometry.

In an alternative embodiment, a mechanical spring is arranged between the tappet and the valve housing, the mechanical spring being able to form the bearing for the freely floating tappet and pre-loading the tappet against the valve housing such that it releases the barrier membrane from the blocking geometry in its zero position. The valve can furthermore have an actuator which acts on the tappet and which is configured such that it can move the tappet out of the zero position against the pre-load of the mechanical spring and can thus press the barrier membrane toward the blocking geometry.

In an embodiment, the mechanical spring is a helical spring which acts as a compression spring and is, for example, a metallic or ceramic helical spring.

In an embodiment, the actuator is a pneumatic actuator. Alternatively, a mechanical or hydraulic actuator can also be provided.

In an embodiment, the pneumatic actuator comprises an actuator membrane which is adjacent to an inflation chamber or surrounds an inflation chamber. The inflation chamber has an interface for the connection of a pneumatic pressure line. The actuator membrane is arranged and configured such that it can press the actuator against the tappet and can thus act on the latter in the active state of the actuator.

In an embodiment, the tappet is in the form of a pin and preferably has a radial flange arranged between its two oppositely disposed ends.

In an embodiment, the tappet is connected to the barrier membrane at one end and to the actuator membrane at the other end. Provision is furthermore made in this embodiment that the mechanical spring engages at the tappet at the side of the flange facing the barrier membrane.

In an alternative embodiment, the tappet is connected to the barrier membrane at one end. Provision is furthermore made in this embodiment that the mechanical spring engages at the tappet at the side of the flange remote from the barrier membrane and that the side of the flange facing the barrier membrane forms a support surface for the actuator membrane.

In an embodiment, the valve housing comprises two parts which are releasably fastened to one another, wherein a first part defines the hollow space for the tappet and a second part defines the fluid chamber, and wherein the barrier membrane is arranged between the two parts. The barrier membrane can in this respect likewise be removed from the first part in an embodiment. The first part in this embodiment is a reusable unit which is not in contact with the fluid path and is thus protected from contamination by the fluid. Only the replaceable barrier membrane and the second part, which is a replaceable reusable unit, come into contact with the fluid.

The barrier membrane and/or the actuator membrane can, for example, be a round silicone disk or a silicone plate.

The valve can be a two-way blocking and/or restricting valve which has exactly one fluid inlet and exactly one fluid outlet.

Against the initially named background, the invention furthermore relates to a blood treatment device having at least one blocking and/or restricting valve in accordance with the invention. The blood treatment device is preferably a dialysis device.

In an embodiment, the valve is arranged in a metering line which opens into the dialysis fluid circuit or into the extracorporeal blood circuit. The valve is preferably arranged in a metering line for a solution of a coagulation-inhibiting agent such as heparin or citrate which opens into the extracorporeal blood circuit.

Figure 2:
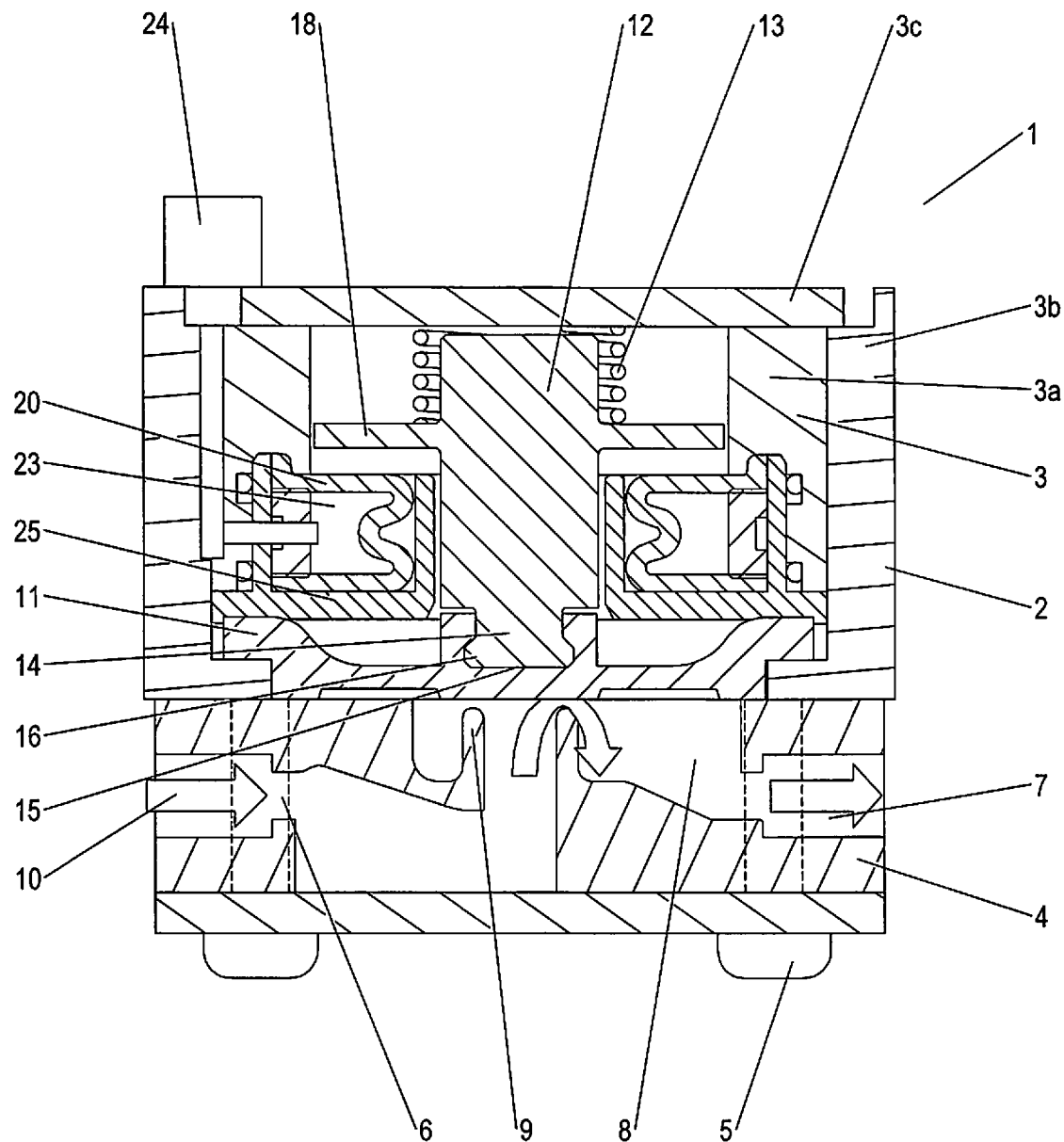

Further details and advantages of the invention result from the embodiments described in the Figures. There are shown in the Figures:

FIG. 1: an embodiment of a normally opened blocking and/or restricting valve in accordance with the invention; and FIG. 2: an embodiment of a normally closed blocking and/or restricting valve in accordance with the invention.

FIG. 1 shows a blocking and/or restricting valve in accordance with the invention which is generally marked by the reference numeral 1.

The valve has a valve housing 2 which comprises a reusable part ("reusable unit") 3 and a disposable part ("disposable unit") 4 releasably fastened thereto. The disposable unit 4 is fastened to the reusable unit 3 using releasable pins 5. The reusable unit 3 in turn comprises an insert 3a which is placed into a cut-out of a machine plate 3b and which is covered by a closure plate 3c.

The disposable unit 4 comprises a fluid path having a fluid inlet 6, a fluid outlet 7 and a fluid chamber 8 arranged therebetween. A blocking geometry 9 is formed within the fluid chamber and is a web which runs around the round chamber inlet opening in the manner of a collar and which projects into the fluid chamber 8. The fluid flow is made recognizable by the arrows 10.

The fluid chamber 8 is bounded by a barrier membrane 11 in the form of a silicone plate at the side disposed opposite the blocking geometry 9. The silicone plate covers a round opening in the wall of the fluid chamber 8 arranged concentrically to the round concentric to the round camera inlet opening.

The silicone plate 11 is inserted releasably into the reusable unit 3 between the insert 3a and the machine plate and closes flush with the disposable unit 4 at all sides of the fluid chamber 8 so that no section of the reusable unit 3 is in contact with the fluid path. The reusable unit 3 is protected from contamination by the fluid in this manner and only the replaceable silicone plate 11 and the replaceable reusable disposable unit 4 come into contact with the fluid.

A hollow space is formed behind the silicone plate 11 in the reusable unit 3 and a pin-like tappet 12 is arranged therein for the deflection of the silicone plate 11. The tappet comprises a radially peripheral flange 18 between its end region 14 (the "blocking side") facing the fluid chamber and its end region 19 (the "actuator side") remote from the fluid chamber. The central axis of the tappet 12 runs through the center of the camera inlet opening. The tappet 12 can be moved linearly to and fro along the central axis within the hollow space and can in this respect be moved toward and away from the fluid chamber. It is held freely floating between the walls of the hollow space by a helical spring 13, for example of metal, with axes of the tappet 12 and of the helical spring 13 being concentric with one another. The helical spring 13 engages the tappet 12 at the side of the flange 18 facing the fluid chamber and in so doing acts as a compression spring. At the other end, the helical spring lies on a projection 17 in the reusable unit 3. A section of the pin-like tappet body arranged at the fluid chamber side of the flange 18 extends within the helical spring 13.

The blocking side 14 of the tappet 12 comprises a holding flange 16 and a receiver 15 for the blocking side 14 of the tappet 12 is molded at the hollow space side at the silicone plate 11, said receiver having an undercut corresponding to the holding flange 16. In this manner, both tensile forces and compressive forces can be transferred from the tappet 12 to the silicone plate 11 in the region aligned with the blocking geometry 9. On the one hand, it is achieved by this arrangement that the silicone plate 11 is pushed in the direction of blocking geometry 9 on a (closing) movement of the tappet 12 directed in the direction of the fluid chamber, which effects a restriction or blocking of the fluid flow in operation of the valve 1 and, on the other hand, it is achieved that the silicone plate 11 is lifted by the blocking geometry 9 on an (opening) movement of the tappet 12 directed away from the fluid chamber, which effects an opening or enlarging of the fluid flow in the operation of the valve 1.

An actuator membrane 20 in the form of a round silicone disk clamped between the cover plate 3c and the insert 3a bounds the hollow space at its end disposed opposite the silicone plate 11. The silicone disk 20 is arranged in parallel with the silicone plate 11 and the center of the silicone disk 20 lies in the axis of the tappet 12.

The silicone disk 20 is also connected to the tappet 12, more precisely to the actuator side 19 of the tappet. For this purpose, the actuator side 19 of the tappet 12 also comprises a holding flange 22 and a receiver 21 is also molded at the hollow space side at the silicone disk 20, said receiver having an undercut corresponding to the holding flange 22. Compressive forces can thus be transferred from the silicone disk 20 to the tappet 12 and the tappet can be held in the region of the center of the silicone disk 20. It is achieved by this arrangement that the tappet 12 executes a (closing) movement directed against the compressive force of the spring 13 and in the direction of the fluid chamber on a deformation of the silicone disk 20 pressing into the hollow space.

An inflation chamber 23 is formed between the silicone disk 20 and the cover plate. On a generation of a fluid pressure in the inflation chamber 23, a balloon-shaped extension (and thus a deformation pressing into the hollow space) of the silicone disk 20 takes place. A connection 24 is worked into the closure plate 3c for the connection of a control system, for example a pneumatic control system. The pneumatic connection in turn lies in the axis of the tappet 12.

If an excess pressure is generated in the inflation chamber 23, the silicone disk 20 presses onto the tappet 12 and moves it against the compressive force emanating from the spring 13 in the direction of the fluid chamber 8, whereby the silicone plate 11 is pressed in the direction of the blocking geometry 9, which effects a restricting or closing of the fluid path. If the excess pressure drops, the spring 13 presses the tappet 12 against the inflation chamber 23, whereby the silicone plate 11 is lifted from the blocking geometry 9, which effects an opening or enlarging of the fluid path. Since the spring 13 lifts the tappet 12 from the fluid chamber 8 and thus lifts the silicone plate 11 from the blocking geometry 9, the valve shown in FIG. 2 is opened in its zero position (on a failure of the control system, where applicable "currentless").

FIG. 2 shows a further embodiment of a blocking and/or restricting valve in accordance with the invention, wherein identical parts or parts of equivalent function are marked by identical reference numerals as is the case in FIG. 1.

The prime difference with respect to the valve shown in FIG. 1 is that the blocking and/or restricting valve shown in FIG. 2 is closed in its zero position (on a failure of the control system, where applicable "currentless").

As regards the construction design, the normally closed valve of FIG. 2 differs from the normally open valve of FIG. 1 in that the mechanical compression spring 13 does not act on the tappet at the side of the flange 18 at the fluid chamber side, but at the side remote from the fluid chamber. The base of the compression spring 13 is therefore not supported against a projection 17 in the hollow space of the reusable unit 3 in the embodiment of FIG. 2, but rather against the cover plate 3c. In contrast, the pneumatic actuator comprising an inflation chamber 23 and an actuator membrane 20 in the present case acts at the side of the flange 18 at the side of the fluid chamber instead of at the actuator side 19. The special configuration of the actuator side with a holding flange 22 can therefore be dispensed with.

The pneumatic actuator in the present case does not comprise a silicone disk as is the case in the embodiment of FIG. 1, but rather an inflatable hose 20 which radially surrounds the tappet 12 and is arranged in the hollow space at the fluid chamber side of the flange 18. A ring-shaped receiver 25 which is open in the direction of the flange is provided in that region of the hollow space in which the projection 17 for supporting the spring 13 is arranged in the embodiment in accordance with FIG. 1 for the reception of this hose 20.

If an excess pressure is generated in the inflation chamber 23 surrounded by the hose 20, the hose inflates and presses against the flange of the tappet so that the latter is pressed in the direction of the closure plate 3c against the compressive force emanating from the spring 13, whereby the silicone plate 11 is lifted from the blocking geometry 9, which effects an opening or enlarging of the fluid path. If the excess pressure drops, the spring 13 in turn presses the tappet 12 in the direction of the fluid chamber 8, which effects a restricting or closing of the fluid path. Since the spring 13 presses the tappet 12 in the direction of the fluid chamber 8 and thus presses the silicone plate 11 toward the blocking geometry 9, the valve shown in FIG. 2 is closed in its zero position (on a failure of the control system, where applicable "currentless").

The connection 24 for a control system, for example a pneumatic control system, to the inflation chamber 23 engages radially at the hose 20.

FIG. 2 does not show the valve 1 in its zero position, but rather for purposes of illustration in a position (which does not occur during operation) in which the tappet 12 is lifted from its zero position despite a lack of inflation of the hose 20.

A central aspect of the invention with regard to both embodiments is that the tappet 12 is arranged in a freely floating manner within the hollow space and the surface of the tappet 12 does not contact a sealing lip such as a sealing ring. Dynamic friction effects such as a delayed response and a disproportional behavior of the tappet in response to a pressure increase ("stick-slip" phenomena), which can in particular be very pronounced on a pneumatic control using a compressible gas, are avoided. The valve 1 in accordance with the invention can be pneumatically regulated in a strictly proportional manner. It is possible due to the proportionality not only to distinguish between two states (closed, opened), but it is rather also possible for the valve to take over the function of a restrictor.

The invention claimed is:

1. A valve having a pneumatic actuator and a valve housing which has a fluid system having a fluid inlet, a fluid outlet, and a fluid chamber arranged therebetween, wherein the fluid chamber comprises a blocking geometry and is bounded by a barrier membrane with respect to the blocking geometry, characterized in that the barrier membrane is connected to a tappet on its side remote from the fluid chamber such that it is pressed toward the blocking geometry and can be lifted by it by a movement of the tappet, with the tappet being arranged in a freely floating manner in a hollow space of the valve housing, characterized in that a mechanical spring is arranged between the tappet and the valve housing, the spring pre-loading the tappet against the valve housing such that it presses the barrier membrane toward the blocking geometry in its zero position, and characterized in that the pneumatic actuator comprises an inflatable hose radially surrounding the tappet, acts on the tappet, and is configured such that it can move the tappet out of the zero position against the pre-load of the mechanical spring and can thus release the barrier membrane from the blocking geometry.

2. A valve in accordance with claim 1, characterized in that the tappet is of pin shape.

3. A valve in accordance with claim 2, characterized in that the tappet is connected to the barrier membrane at one end, with provision furthermore being made that the mechanical spring engages at the tappet at the side of the flange remote from the barrier membrane and the side of the flange facing the barrier membrane forms a support surface for the actuator membrane.

4. A valve in accordance with claim 1, characterized in that the valve housing comprises two parts which are releasably fastened to one another, with a first part defining the hollow space for the tappet and with a second part defining the fluid chamber, and with the barrier membrane being arranged between the two parts.

5. A blood treatment device having valve in accordance with claim 1, wherein the blood treatment device is a dialysis device.

6. A blood treatment device in accordance with claim 5, characterized in that the valve is arranged in a metering line which opens into the dialysis fluid circuit or into the extracorporeal blood circuit.

7. A valve in accordance with claim 1, characterized in that the tappet is of pin shape and has a radial flange arranged between its two oppositely disposed ends.

8. A valve in accordance with claim 7, characterized in that the tappet is connected to the barrier membrane at one end, with provision furthermore being made that the mechanical spring engages at the tappet at the side of the flange remote from the barrier membrane and the side of the flange facing the barrier membrane forms a support surface for the actuator membrane.

9. A blood treatment device in accordance with claim 5, characterized in that the valve is arranged in a metering line which opens into the dialysis fluid circuit or into the extracorporeal blood circuit, with the blocking and/or restricting valve being arranged in a metering line for a solution of a coagulation-inhibiting agent which opens into the extracorporeal blood circuit.

* * * * *